United States Patent [19]

Riley

[11] Patent Number: 5,540,901

[45] Date of Patent: *Jul. 30, 1996

[54] STERILIZATION TRAY SYSTEM FOR SURGICAL INSTRUMENTS

[75] Inventor: Edward D. Riley, Falmouth, Me.

[73] Assignee: Riley Medical, Inc., Auburn, Me.

[ * ] Notice: The term of this patent shall not extend beyond the expiration date of Pat. No. 5,424,048.

[21] Appl. No.: 368,365

[22] Filed: Jan. 4, 1995

Related U.S. Application Data

[63] Continuation-in-part of Ser. No. 212,950, Mar. 15, 1994, Pat. No. 5,424,048.

[51] Int. Cl.$^6$ ............................... A61B 19/02; A61L 2/06; A61L 2/16
[52] U.S. Cl. ........................... 422/300; 206/370; 206/438; 220/676; 220/505
[58] Field of Search ..................................... 422/300, 297, 422/310; 206/370, 438; 220/676, 505

[56] References Cited

U.S. PATENT DOCUMENTS

| | | |
|---|---|---|
| 4,798,292 | 1/1989 | Hauze . |
| 4,854,475 | 8/1989 | Riihimaki et al. . |
| 5,098,676 | 3/1992 | Brooks, Jr. . |
| 5,165,539 | 11/1992 | Weber et al. . |
| 5,174,453 | 12/1992 | Stoeffler . |
| 5,384,103 | 1/1995 | Miller ................... 422/297 X |
| 5,424,048 | 6/1995 | Riley ........................ 422/300 |
| 5,433,930 | 7/1995 | Taschner .................. 422/300 |

FOREIGN PATENT DOCUMENTS

| | | |
|---|---|---|
| 2693101 | 7/1992 | France . |
| 3534897 | 4/1987 | Germany . |
| 9105867 | 9/1991 | Germany . |
| 4103146 | 3/1992 | Germany . |

Primary Examiner—Robert Warden
Assistant Examiner—E. Leigh Dawson
Attorney, Agent, or Firm—Cesari and McKenna

[57] ABSTRACT

A modular sterilization tray system for medical instruments comprises a rigid, substantially rectangular case having a pair of opposite side walls, a pair of opposite end walls and a bottom wall. A plurality of vertical columns of vertically spaced apart uniform size holes are formed in the case side walls and end walls. Also, one or more substantially rectilinear instrument trays are provided for placement in the case, the length and width dimensions of each of the trays being directly related to the spacing of the columns of holes in the case side and end walls such that one or more trays may be positioned within the case so as to be bracketed by selected columns of holes. The system also includes fixtures for positioning in selected holes of the bracketing columns of holes for fixing the position of one or more trays at a selected elevation in the case and fixation brackets for variously shaped instruments placed in the trays.

29 Claims, 5 Drawing Sheets

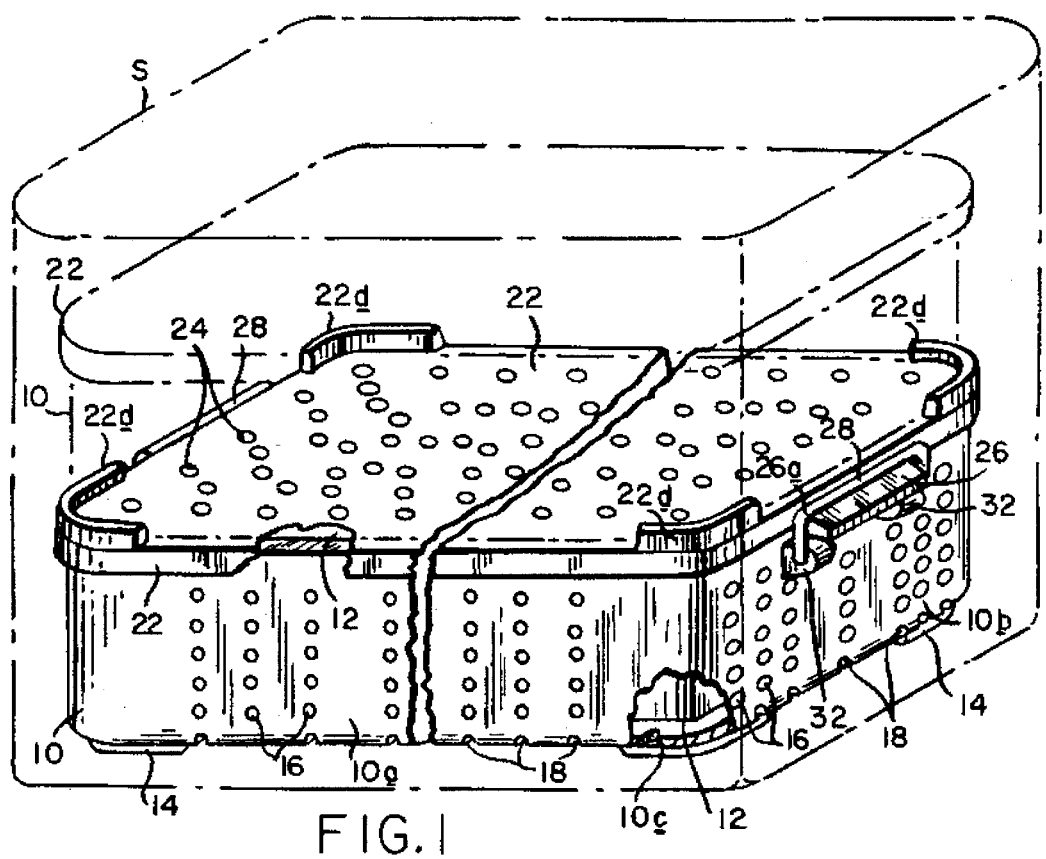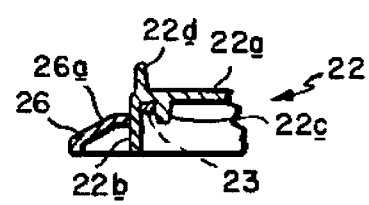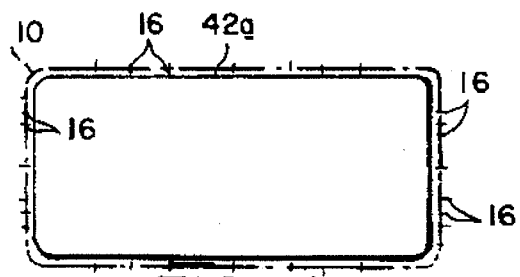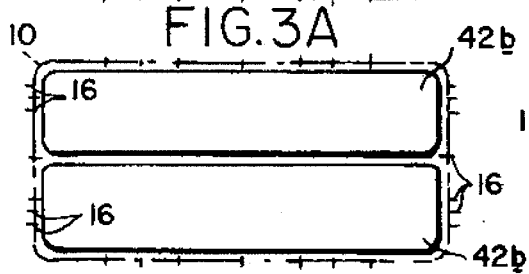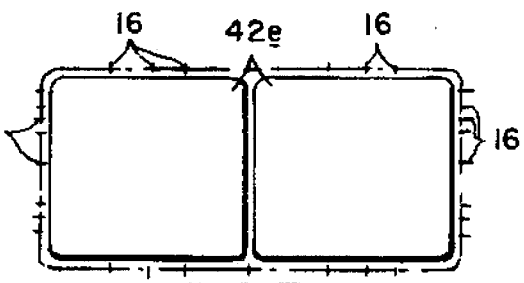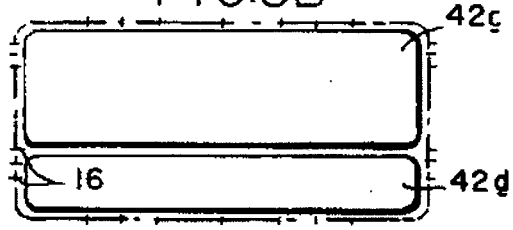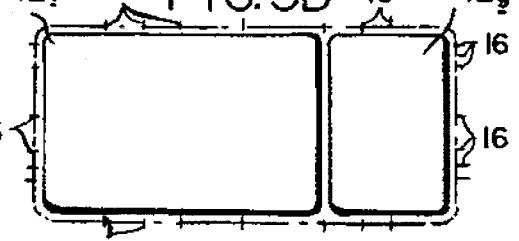

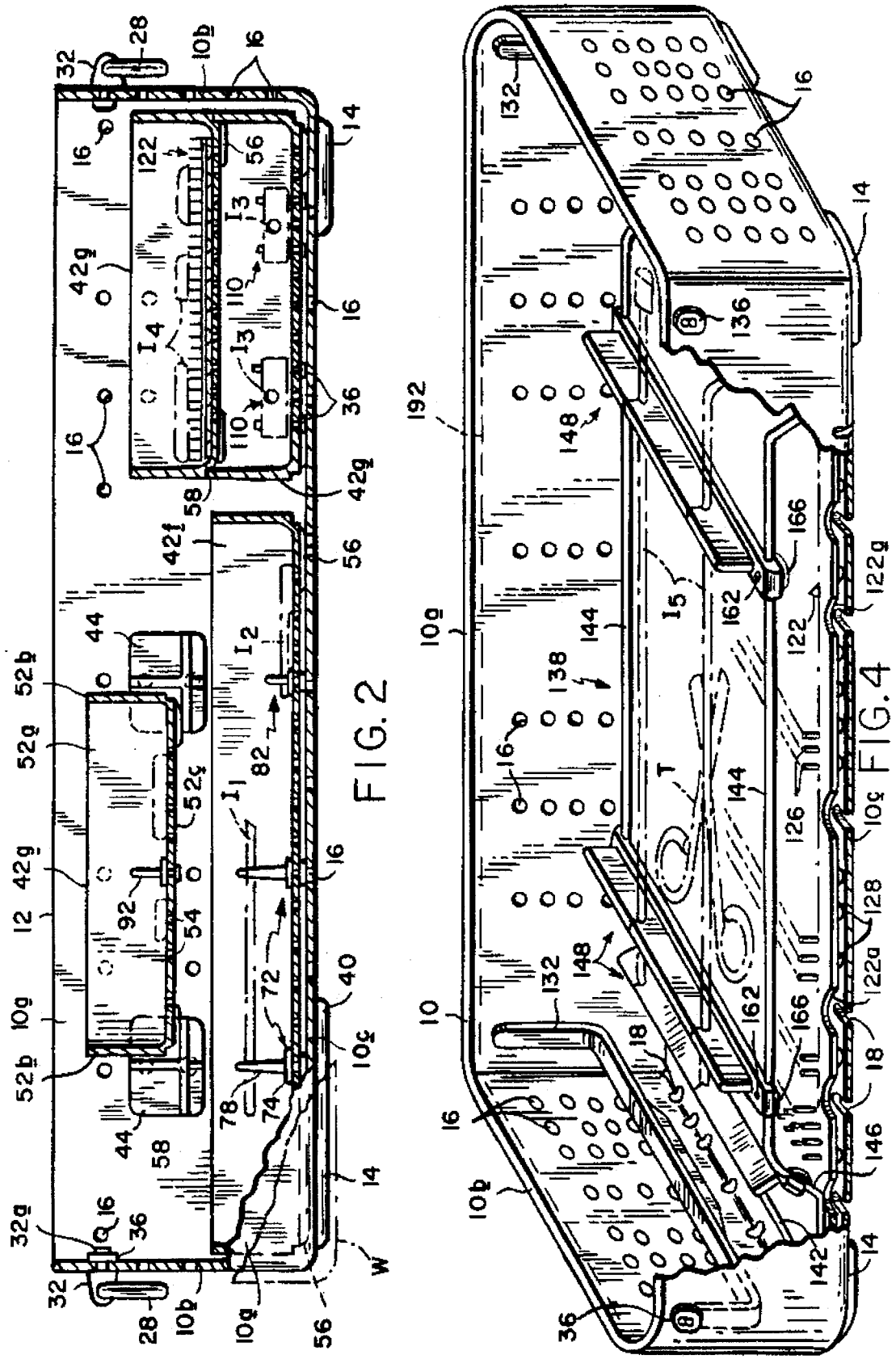

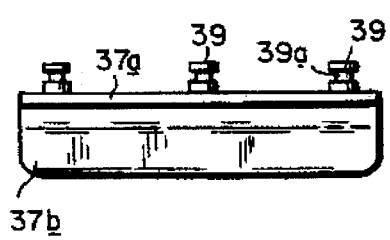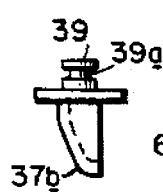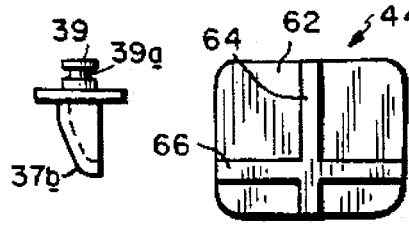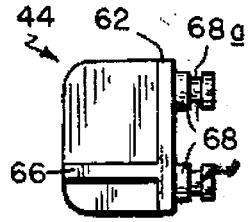
FIG.5A  FIG.5B  FIG.6A  FIG.6B
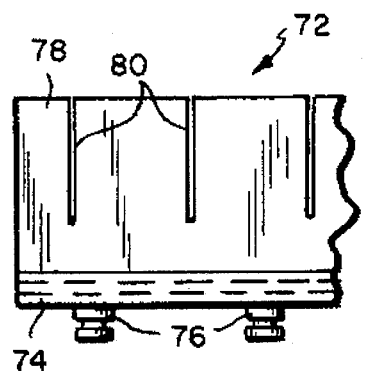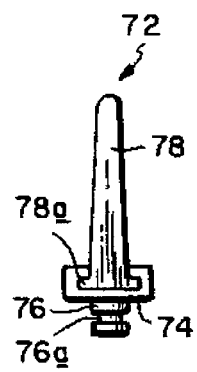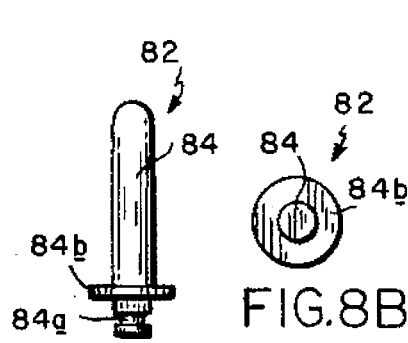
FIG.7A  FIG.7B  FIG.8A  FIG.8B
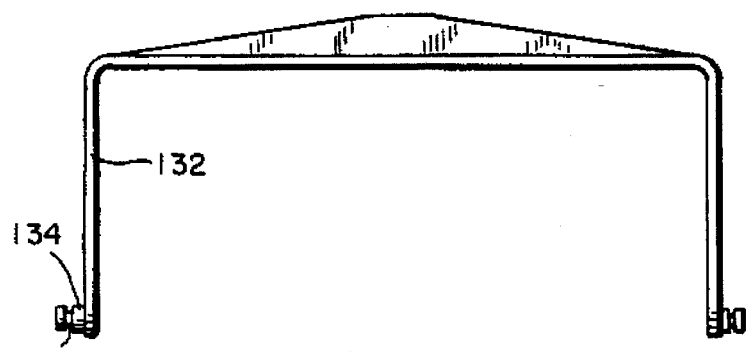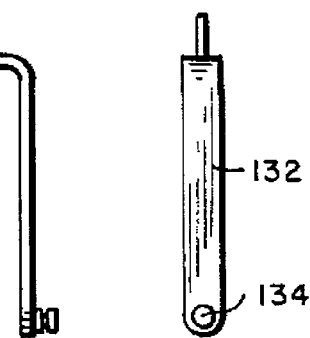
FIG.9A  FIG.9B
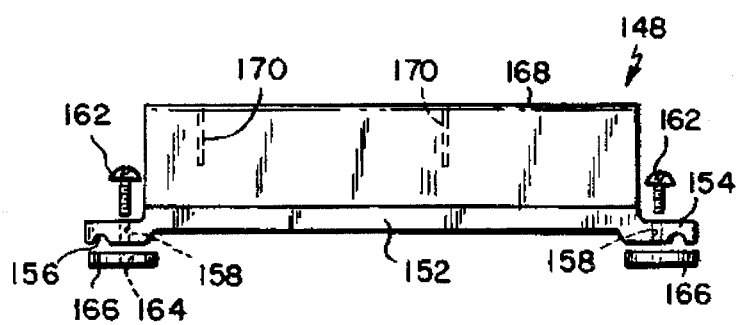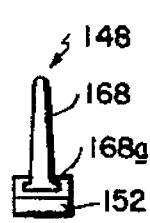
FIG.10A  FIG.10B

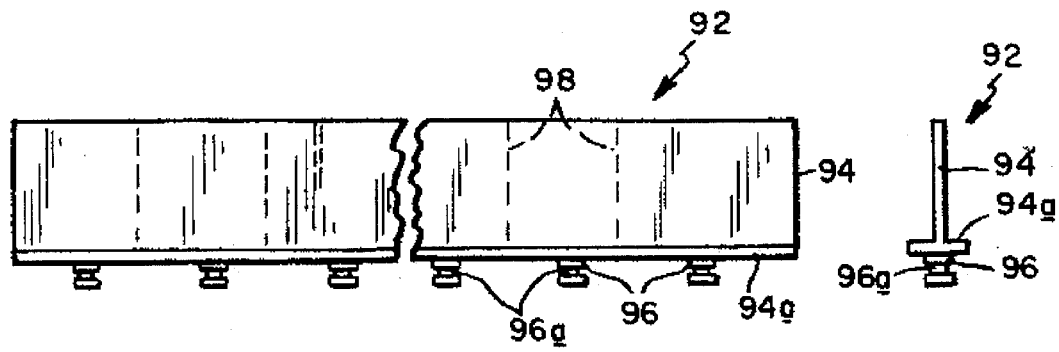
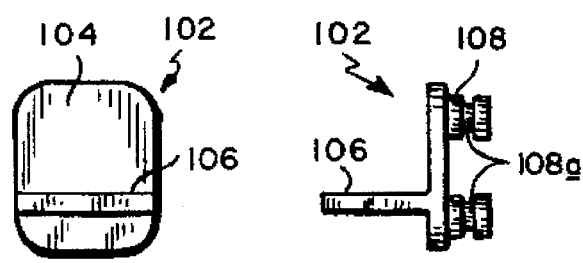
FIG.11A  FIG.11B
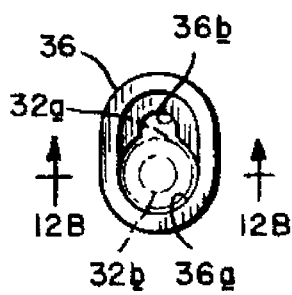
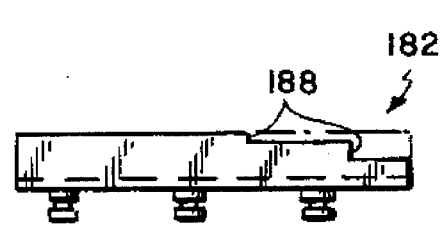
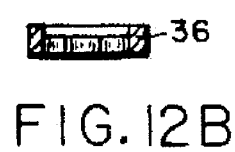
FIG.12A  FIG.13A  FIG.13B
FIG.12B
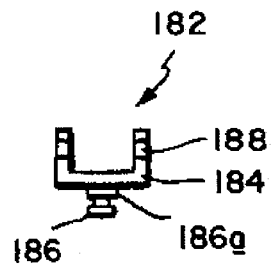
FIG.14A  FIG.14B
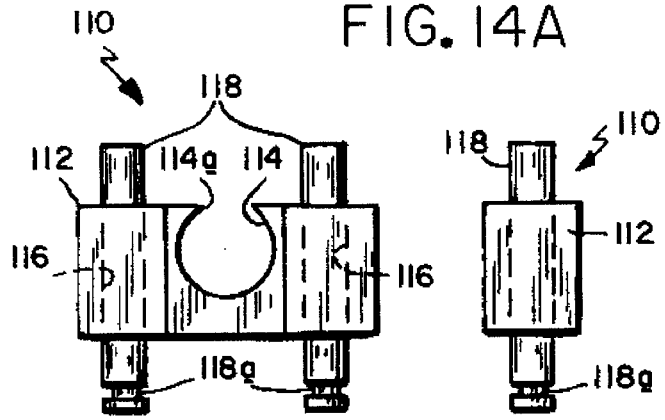
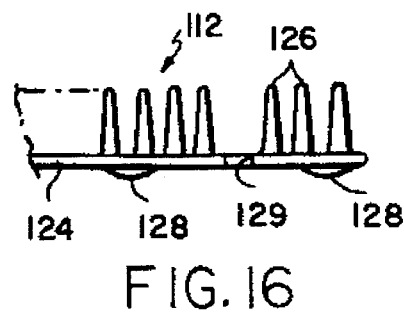
FIG.15A  FIG.15B  FIG.16

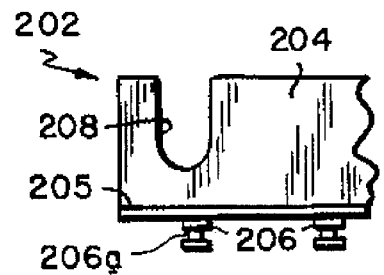 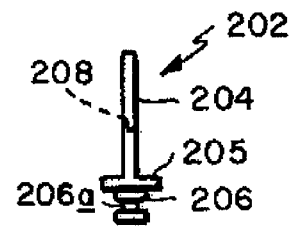
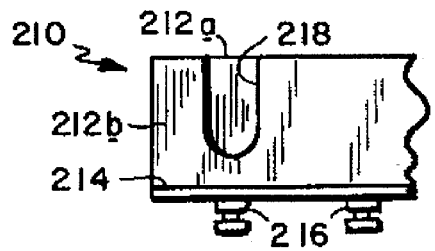 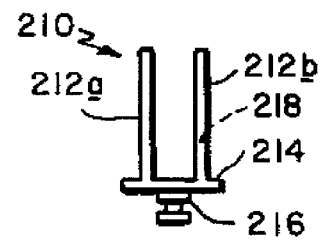
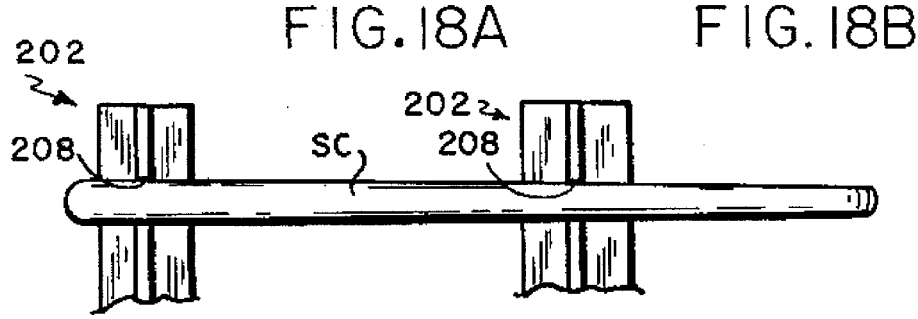
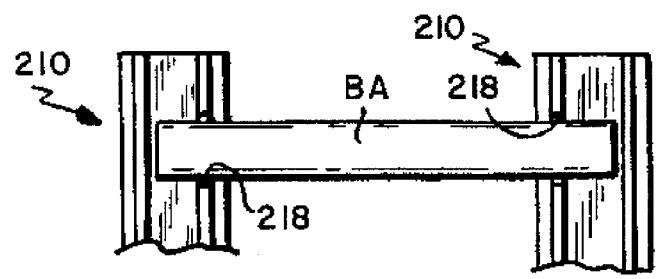
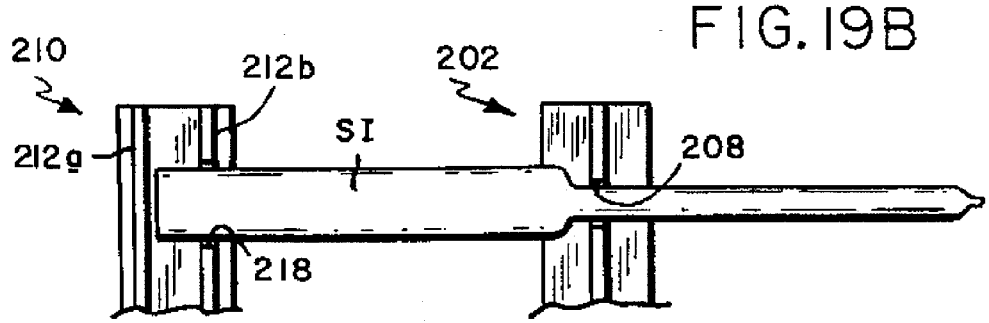

STERILIZATION TRAY SYSTEM FOR SURGICAL INSTRUMENTS

RELATED APPLICATION

This application is a continuation-in-part of Ser. No. 08/212,950, filed Mar. 15, 1994, now U.S. Pat. No. 5,424,048.

This invention relates to the sterilizing of medical and surgical instruments and materials. It relates more particular to an improved tray system to facilitate sterilizing, delivering and presenting surgical instruments and materials in a sterile condition prior to surgery and to preventing contamination from said instruments following surgery.

BACKGROUND OF THE INVENTION

It is normal procedure to provide appropriate types and quantities of surgical instruments and materials for a specific surgical procedure as a unitary package that has previously been sterilized. Prior to or during an operation, the instruments and materials are removed from the package and laid out on a Mayo table or other surface so that they are readily accessible to the surgeon performing the operation.

A typical instrument package may include a basket or tray in which the instruments are placed. Fixating means such as a finger mat or post may be provided to fix the positions of the instrument in the basket or tray so that the instruments do not become co-mingled or damaged when the basket or tray is moved about.

As shown in U.S. Pat. Nos. 4,643,303, 4,671,943 and 4,798,292, the basket or tray may be a rigid box-like container with a removable cover to protectively enclose the instruments. Also, in some cases, fixation modules are provided to segregate and fix the positions of the instruments; see, for example, U.S. Pat. No. 4,643,303. Invariably, however, there is little flexibility in the placement of those modules within the container and only a single layer of trays is allowed in the container. This limits the number and variety of instruments that may be sterilized in the container at one time.

The prior sterilizing apparatus employing such containers are disadvantaged also because openings for the passage of steam or other sterilant are only present in the top and bottom walls of the container. There is no provision for lateral circulation of fluid sterilant to and from the container. Therefore, the sterilization is slower than need be.

This factor also limits the ability of the user to stack instrument-fixating modules within the prior containers without further inhibiting proper circulation of the sterilant through the container.

SUMMARY OF THE INVENTION

Accordingly, it is an object of the present invention to provide an improved sterilization tray system for medical instruments.

Another object is to provide such a system which has a perforate case for containing instrument trays which can be arranged in a variety of different positions and elevations within the case.

A further object of the invention is to provide a system of this type which enables sterilization of instruments contained by the system in a minimum amount of time.

Still another object is to provide a sterilization tray system which can be used to sterilize, deliver and present medical instruments prior to a surgical procedure using the instruments and as a repository for contaminated instruments following the procedure to avoid adverse affects from such contamination.

Other objects will, in part, be obvious and will, in part, appear hereinafter.

The invention accordingly comprises the features of construction, combination of elements and arrangement of parts which are exemplified in the following detailed description, and the scope of the invention will be indicated in the claims.

Briefly, my improved sterilization tray system comprises an outer box-like case having columns of holes in the case side and end walls as well as the case bottom wall through which steam or other sterilant may circulate both vertically and laterally through the case. These holes also serve as anchoring points for a variety of different brackets and fixtures to be described in detail later for retaining various different instruments and instrument trays within the case.

The positions of the columns of holes are directly related to the dimensions of the trays to enable the trays to be retained at many different positions and elevations within the case without interfering materially with the circulation of sterilant through the case. Thus, a maximum number of instruments of different types for a given surgical procedure may be sterilized, delivered and presented at one time.

The system also includes a low cost perforate liner for the case to enable the case to receive contaminated instruments following the procedure so that those instruments can remain isolated until they can be cleaned and re-sterilized, thereby minimizing the chances of infection from said instruments.

BRIEF DESCRIPTION OF THE DRAWINGS

For a fuller understanding of the nature and objects of the invention, reference should be had to the following detailed description, taken in connection with the accompanying drawings, in which:

FIG. 1 is an isometric view with parts broken away showing a tray system incorporating my invention;

FIG. 1A is a fragmentary sectional view showing a portion of the cover component of the FIG. 1 system in greater detail;

FIG. 2 is a longitudinal sectional view on a larger scale showing various tray components of the FIG. 1 system;

FIGS. 3A to 3E are a diagrammatic views showing some possible tray layouts in the FIG. 1 system;

FIG. 4 is an isometric view with parts broken away illustrating other components of the tray system in greater detail;

FIGS. 5 to 15 are front (A) and side (B) views, respectively, of various fixtures and brackets comprising the FIG. 1 system;

FIG. 16 is a fragmentary side elevational view of a finger mat used in the FIG. 1 system;

FIGS. 17A and 17B are views similar to FIGS. 5A and 5B of a different bracket embodiment, and FIGS. 18A and 18B are views similar to FIGS. 17A and 17B of yet another bracket embodiment, and FIGS. 19A and 19C are fragmentary plan views of additional bracket embodiments.

DETAILED DESCRIPTION OF ILLUSTRATIVE EMBODIMENTS

Referring to FIGS. 1 and 2 of the drawings, my tray system comprises a rigid, generally box-like outer case 10 having a pair of mirror image side walls 10a, pair of mirror image end walls 10b and a bottom wall 10c defining a generally rectangular interior space 12. Preferably, case 10 is provided with integral legs 14 at the four corners of the case so that the case bottom wall 10c is spaced above the surface on which it is placed. The case should be made of a material well able to withstand sterilization, e.g., polyphenyl sulphone. Typically, case 10 may be about twenty one inches long, ten inches wide and five inches high.

Formed in the side and end walls of case 10 are columns of equal size holes 16. Thus, the case side walls 10a contain a column of five holes 16 located midway along the case and three columns of holes spaced on each side of that middle column. Likewise, each case end wall 10b has a column of five holes midway along the end wall and three columns of holes 16 on each side of that middle column. There is also an array of holes 16 distributed uniformly over the surface of the case bottom wall 10c, certain columns and rows of that array being aligned with the columns of holes in the case 10 side and end walls. The various holes 16 allow for circulation of steam or other sterilizing fluid through the interior of the case. Also, as will be described in more detail later, the positions of the holes are related directly to the dimensions of the various tray components comprising the FIG. 1 system so they can function as anchoring points for the brackets and fixtures used to locate those trays within the interior space 12 of case 10.

Preferably also, a series of corner slots 18 are spaced around the perimeter of the case bottom wall 10c. These provide additional avenues for steam circulation within the case adjacent to the case bottom wall 10c.

The open top of case 10 may be closed by a cover 22. As shown in FIG. 1A, the cover has a top all 22a with a peripheral depending skirt 22b arranged to engage over the rim of the case. There is also a depending flange 22c extending down from cover wall 22a just inboard skirt 22b. This flange engages inside the case side and end walls to help locate the cover 22 relative to the case. Also, in those application that demand a sealing engagement of the cover 22 with case 10, a gasket 24 may be provided between skirt 22b and flange 22c as indicated in phantom at 24 in FIG. 1A.

The cover top wall 22a contains an array of round holes 24 similar to holes 16 described above. Holes 24 may be arranged more or less in the same pattern as the holes 16 in bottom wall 10c to allow the passage of steam or other fluid sterilant to and from the interior space 12.

As shown in FIGS. 1 and 1A, a pair of lifting handles 26 are present at the opposite ends of cover 22. Also, in those cases where it is desirable to releasably secure cover 22 to case 10, the handles 26 may cooperate with retaining means on the ends of case 10 to releasably lock the cover to the case. In the illustrated tray system, the retaining means comprise a wire bail 28 having opposite in-turned ends which are swingably engaged in a pair of brackets 32. The brackets 32 are provided with integral posts 32a arranged to project through holes 16 in the case ends walls 10b just below and adjacent to the cover handles 26. The brackets 32 are firmly anchored to the end walls of case 10 by means of locking rings 36. As shown in FIG. 12A and 12B, each ring 36 includes a relatively large diameter opening 36a whose diameter is slightly larger than that of post 32a. That opening 36a leads into a smaller opening 36b which is arranged to tightly receive a necked down or grooved portion 32b of post 32a inside the case so that the brackets 32 and the bail are firmly anchored to the case.

Cover 22 is secured to case 10 by swinging the bails 28 up over the cover handles 26 as shown in FIG. 1. Preferably, grooves 26a are present at the tops of handles 26 into which bails 28 may seat to retain the bails in their locked positions as shown. Obviously, the bails 28 may also function as handles for case 10 when disengaged from the cover.

When a lockable cover is not needed for case 10, the bails 28 may be replaced by the handles 37 depicted in FIGS. 5A and 5B. Each handle includes a rear wall 37a and a shelf 37b projecting forwardly from the flange. Also, extending rearwardly from the flange is a series of spaced apart posts 39, the spacing of the posts being the same as the spacing of the holes 16 in the three innermost hole columns in the end walls 10b of case 10. Posts 39 have reduced diameter necks 39a arranged to receive the locking rings 36 described above to anchor the handles to the case 10.

Also as shown in FIG. 1, cover 22 is preferably provided with raised corner flanges 22d to facilitate stacking the covered cases 10. When so stacked, the flanges 22d of each case engage around the lower edge margins of the case 10 next above in the stack, with the legs 14 of that upper case resting on the cover 22 such that the bottom wall 10c of the upper case is spaced from the cover top wall 22a of the lower case. Thus, steam is free to circulate between the two cases and enter and leave the cases through the openings 16 in the opposing walls thereof.

In use, a stack of such cases may be placed in sterilizing apparatus S as shown in phantom in FIG. 1. The apparatus S may be an autoclave or a chemical sterilizer. Alternatively, the apparatus may be enclosed within a valved container such as the one disclosed in my U.S. Pat. Nos. 4,748,003 and 5,097,865 which is, in turn, placed in an autoclave or other sterilizer. As described in those patents, after the sterilizing process, the tray system may remain hermetically sealed inside the valved container and, therefore, in a sterile condition for a prolonged period until needed.

Such sterility can also be maintained to a somewhat lesser degree by covering case 10 and its contents with a bag or wrap made of a material such a muslin, toweling, treated paper or a nonwoven material such as that sold under the brand name Tyvec which may be penetrated by steam during the sterilization process, but which provides a barrier to micro-organisms after sterilization. A fragment of such an outer wrap is shown in phantom at W in FIG. 2.

When such a wrap is employed, and the tray system is sterilized in a so-called gravity steam sterilizer in which air leaves the sterilizer and case 10 under the influence of gravity rather than a vacuum, the wrap W may tend to cling to the bottom wall 10c of the case. This slows the escape of air from the case thereby slowing the sterilization process. To avoid this, one or more depending ribs 40 (FIG. 1) may be provided at the underside of case bottom wall 10c to function as a spacer for the wrap W at that location. Typically, the ribs 40 may extend between opposite corners of bottom wall 10c forming the letter X.

It has also been observed that the presence of trapped air in the case 10 during sterilization is minimized when the corner slots 18 are present. Apparently, wrap W is not pressed tightly against the case at the lower corners thereof so that the trapped air is free to exit through the slots 18. Therefore, either the slots 18 or the ribs 40 may be used to avoid the problem of trapped air during gravity sterilization.

Refer now to FIGS. 2 and 3, the present system also includes a variety of different trays for holding various surgical instruments and materials. These trays are preferably made of the same material as case 10 and they are designed so that they can be arranged in a variety of different configurations inside the case as shown in FIGS. 3A to 3E.

The different trays are more or less the same except for their dimensions.

As shown in FIG. 3A, the system includes a full size tray 42a which is arranged to fit snugly inside the case, occupying almost the entire floor area thereof; however, some inside end clearance remains for inside case handles to be described later. There is also a pair of trays 42b which are the same length as tray 42a but slightly less than half the width thereof so that two such trays can sit side by side in case 10 as shown in FIG. 3B. The system further includes a third type of tray 42c which is the same length as tray 42a but only two-thirds as wide and another full length tray 42d which is only one-third the width of tray 42a; trays 42c and 42d are illustrated in FIG. 3C. My system also includes a pair of trays 42e shown in FIG. 3D which are the same width as tray 42a but only about half as long. Finally, there are trays 42f and 42g shown in FIG. 3E which have the same width as tray 42a but are, respectively, about two-thirds and one-third as long as that tray. All of the trays 42a through 42g can be laid out in case 10 as shown in FIG. 3A to FIG. 3E or they can be used separately or in other combinations that will fit inside case 10.

It should also be understood that the trays 42 may be used separately from the case 10 to carry surgical instruments and they may be provided with lids similar to cover 22. However, such lids are normally not on the trays being sterilized within case 10 because the lids may slow the sterilization process.

As shown in FIGS. 3A to 3E, the locations of holes 16 in case 10 are related to the dimensions of the trays 42 so that the various trays can be fixed at various locations in the case 10 by brackets or fixtures mounted to the case 10 through the holes 16. More particularly, the columns of holes are arranged so that certain columns (or the corresponding columns in the case bottom wall) bracket the full length trays depicted in FIGS. 3B and 3C at different tray positions across the case. For example, fixtures sited at the holes 16 in the two columns bracketing the center column of holes in each case 10 end wall may fix two trays 42d at each side of case 10 or one tray 42d at the case longitudinal centerline. Similar fixtures at any one of those columns of holes will locate either tray 42c or tray 42d at the position shown in FIG. 3C. Fixtures at the center columns of holes in the case end walls will locate a tray 42b at either side of case 10.

In similar fashion, fixtures in the columns of holes 16 in the case side walls (or the corresponding bottom wall holes) may fix the positions of trays 42a to 42g at different locations along the case. For example, fixtures at the center column of holes in FIG. 3D will locate a tray 42a at one or the other end of case 10, and so on.

It should be obvious also that locating the fixtures at different holes in a column of holes in the case side and end walls directly affects the height in the case of the supported tray. Thus several trays can be positioned at different elevations within case 10. Resultantly, with my tray system, a very wide variety of tray placements within case 10 is possible. Furthermore, this flexibility does not adversely affect the circulation of steam through the case and trays during the sterilization process.

In FIG. 2, case 10 contains one tray 42f at the bottom of the case and a pair of stacked trays 42g also resting on the bottom of the case. There is also a third tray 42g supported above tray 42a by corner support brackets 44. Each tray includes a pair of side walls 52a, a pair of end walls 52b and a bottom wall 52c, the last mentioned wall containing an array of holes 54 equal in size to holes 16 described above and through which steam or other sterilant may circulate. Also, feet 56 extend down from the tray bottom wall 52c at the four corners thereof to space the bottom wall above the surface that supports the tray. The feet 56 raise the bottom wall of each tray from the surface to assure good steam circulation through the bottom wall holes and to provide clearance for various fixtures that may be secured to the bottom wall at those holes as will be described.

Preferably, a groove or notch 58 extends around the perimeter of the tray bottom wall 52c to provide a flat surface for seating on the rim of the underlying tray so that the trays can be stacked stably as shown in FIG. 2. The relative heights of the illustrated trays 42 in case 10 are such that two such trays can be stacked one over the other. However, it should be understood that case 10 may be made deeper to accommodate a stack of three or more such trays.

Refer now to FIGS. 6A and 6B which depict the corner bracket 44. Each corner bracket includes a rear wall 62 and vertical and horizontal dividers 64 and 66, respectively, projecting out from wall 62 so as to form a cross more or less, with one of the vertical arms of the cross being shorter than the other. Also, the bracket includes a pair of posts 68 projecting rearwardly frown wall 62. Each post has a reduced diameter segment 68a which may be engaged by a locking ring 36 described above.

Each bracket 44 may be anchored to a wall of case 10 by inserting the posts 68 through holes 16 at the appropriate height on the relevant wall as shown in FIG. 2 and engaging fasteners 36 to the grooved ends of posts 68 projecting through those holes at the outside of the case. Thus, four such brackets 44 may be anchored to the opposite side walls 10a of case 10 to support tray 42g above tray 42f as shown in FIG. 2. Furthermore, by turning the brackets upside down from their positions shown in FIG. 2, the tray 42g may be supported at a slightly higher elevation in case 10 if that is desirable, for example, to clear material contained in the underlying tray 42f.

Also, it should be apparent that each bracket 44 is designed to support two trays at the same time. For example, the right hand bracket 44 in FIG. 2 may support the adjacent ends of two half length trays 42e as shown in FIG. 3D.

My system also includes various brackets and fixtures to fix the positions of the instruments and materials in the trays 42. Thus, the tray 42f in FIG. 2 includes a pair of upstanding instrument supports 72 for fixating one or more relatively long instruments $I_1$ such as scalpels, picks, etc. These supports may come in various lengths to fit the different trays 42. As shown in FIGS. 7A and 7B, each support 72 includes a rigid slide 74 having a pair of posts 76 projecting from the rear face of the slide. Each post has a reduced diameter neck or groove 76a for receiving a locking ring 36 described above. The posts 76 are spaced apart a distance equal to the distance between holes 16 in the bottom wall of a tray 42 or case 10 so that the slide can be anchored to that wall in the same manner as bracket 62.

Secured to slide 74 is an upstanding blade 78 having a flange 78a extending along its lower edge for slidably engaging in slide 74. The blade 78 is made of a resilient material able to withstand sterilization such as silicone rubber. Vertical slits 80 may be spaced along the length of blade 78 or the blade may simply be sliced with a knife as needed so that instruments $I_1$ may be pushed down into the slots to fixate those instruments as shown in FIG. 2. Note that since the tray 42f (as well as the other trays 42) include depending feet 56, the tray bottom wall 52c is spaced above wall 10c of case 10 to provide clearance for the ends of posts 76 and the locking rings 36 that project below the tray. Further, as stated above, the spacing of the tray bottom wall from the bottom of case 10 by legs 56 assures good circulation of steam to and from the tray.

The tray 42f in FIG. 2 also contains a second fixture for fixating certain other medical instruments, to wit: a removable post 82 which projects up from the tray bottom wall. Post 82 is suitable for securing instruments containing a hole or an eye, e.g., scissors. Post 82, which is shown in detail in FIGS. 8A and 8B, comprises a generally cylindrical post member 84 having a reduced diameter neck segment or groove 84a at one end for attaching the locking ring 36 described above. Spaced along the post from groove 84a is a flange 84b. The post may be anchored to the bottom wall of tray 42f or any other tray by inserting the grooved end of the post through an appropriate hole 54 in the tray bottom wall and locking it there by a locking ring 36. Of course, post 82 may also be secured in the same way to a case 10 bottom or side wall through holes 16 therein.

Still referring to FIG. 2, sometimes it is desirable to divide the interior of a given tray 42 to separate instruments or articles therein. Accordingly, my tray system includes dividers one of which is shown generally at 92 in the left hand tray 42g in FIG. 2. As best seen in FIGS. 11A and 11B, each divider 92 comprises an upstanding blade 94 having bottom a flange 94a so that the divider has the general shape of an inverted letter T. Posts 96 are spaced apart along the length of the flange a distance corresponding to the spacing of the holes 54 in trays 42 and the holes 16 in case 10. Each post has a reduced diameter neck or groove 96a for attachment of a locking ring 36 described above.

Preferably, divider 92 is a unitary product molded of a rigid plastic material able to withstand sterilization. It may be made in a standard length somewhat less than the width of case 10 and be formed with a series of score lines or parting lines 98 spaced along its length so that by breaking the divider at one of the score lines 98, the divider may be fitted to any one of the trays 42 comprising applicant's tray system. Also, if desired, several such dividers may be arranged to form "corrals" in trays 42 and in case 10.

Referring now to FIGS. 13A and 13B, shown there is another type of tray bracket indicated generally at 102. It is somewhat similar to bracket 44 described above except that it does not inhibit lateral movement of the tray and only supports one tray. Bracket 102 comprises a generally rectangular rear wall 104 with a rectangular flange 106 projecting forwardly from the rear wall near the bottom thereof. A pair of posts 108 extends from the rear face of flange 104, the posts being spaced apart a distance comparable to the spacing of the holes 16 in case 10. Reduced diameter necks or grooves 108a are provided on the posts 108 to receive locking rings 36 described above to anchor the bracket to a case 10 wall. For example, a pair of the brackets 102 may be mounted at laterally spaced-apart locations to one of the case end walls 10b to support one end of a tray 42e whose opposite ends may be supported by a pair of brackets 44 mounted to the case side walls 10a at the center columns of holes 16 therein; see FIG. 3D.

Also, bracket 102, like bracket 44, may be turned upside down to alter the height in case 10 of the tray which it supports.

Still referring to FIG. 2, barrel-shaped instruments such as indicated at I₃ in FIG. 2, e.g., endoscopes, may be fixed in a given tray 42 by means of pairs of fixtures 110 shown in the right hand bottom tray 42g in FIG. 2. As best seen in FIGS. 15A and 15B, each fixture 110 comprises a rectangular block 112 of resilient material such as silicon rubber. The block contains a lateral cylindrical cut-out 114 having an open mouth 114a at the upper surface of the block. A pair of vertical passages 116 are formed on opposite sides of cut-out 114 for receiving a pair of posts 118 which project below block 112. The corresponding lower end segments of posts 118 contain grooves 118a for receiving the locking rings 36 described above. Posts 118 are spaced apart a distance corresponding to the spacing of the holes 54 at the bottoms of trays 42 and to the spacing of the holes 16 in case 10 so that the fixture 110 can be anchored to one of those walls by inserting the grooved ends of the posts through the appropriate holes and installing the locking rings 36 at the underside of the tray or case. As described previously, the legs 56 on the trays and the legs 14 on the case provide clearance for the projecting ends of the posts and the locking rings.

Sometimes delicate instruments and other articles 14 may be fixated within a tray 42 or case 10 simply by means of a finger mat such as the mat 122 shown in the right hand upper tray 42g in FIG. 2 and in FIG. 16. Mat 122 may be made of a resilient material such as rubber and comprises a web-like base 124 with a multiplicity of upstanding resilient fingers 126 uniformly distributed on the base. Also, formed integrally at the underside of base 124 is an array of hemispherical bosses or nubs 128 which space the mat 122 above the bottom wall of the tray or case so that steam and air can circulate freely between the mat and those walls. If desired, an array of openings 129 may be provided in mat 124 so that steam can circulate through the mat. These holes 129 may be arranged to be aligned with or offset from the holes 54 in the bottom walls of trays 42 or the holes 16 in the bottom wall of case 10.

Refer now to FIG. 4 which shows a case 10 with a finger mat 122 overlying substantially the entire bottom wall 10c of the case. Preferably, the mat 122 for the case has scalloped edges 122a to expose the corner slots 18 in the case so that air and steam are free to pass through those slots during the sterilization process. As noted previously, the finger mat 122 has bosses 128 at its underside to space the mat from the case bottom wall 10c. Medical instruments e.g., scissors T, may be placed on mat 122 with the mat fingers 126 fixing the positions of the instruments.

The case 10 depicted in FIG. 4 is equipped with inside handles 132 at the ends of the case. These may be used in lieu of the lid locking handles 28 depicted in FIGS. 1 and 2 and the handles 37 shown in FIGS. 5A and 5B when space is at a premium inside an autoclave or other sterilizing apparatus S (FIG. 1). As shown in FIGS. 9A and 9B, each handle 132 is a generally U-shaped member whose length corresponds to the inside width of case 10. A pair of posts 134 project out laterally from opposite ends of member 132 which posts are arranged to extend through holes 16 formed in the side walls 10a of case 10 adjacent to the case end walls. The posts 134 have reduced diameter necks or grooves 134a arranged to receive locking rings 36 described above to pivotally secure the handles 132 to the case.

The case 10 depicted in FIG. 4 also contains a instrument rack shown generally at 138 which may rest on the bottom wall 10c of the case or on mat 122. The rack 138 is designed particularly to support relatively long instruments 15 such as laproscopic instruments, etc., within the case. Rack 138 includes a pair of mirror-image, generally C-shaped end sections 142 which extend substantially the full width of case 10 and a pair of long, parallel side rails 144. The ends of the side rails are joined to the end sections by way of angled rail segments 146 which extend up from the end sections at an angle of about 45° so that the side rails 144 are raised above the end sections by about three inches.

Extending between the side rails 144 is one or more instrument supports shown generally at 148 shown in detail in FIGS. 10A and 10B. As seen in those figures, each support comprises a relatively long rigid slide 152 having a pair of tabs 154 extending longitudinally from opposite ends of the slide. Each tab 154 is provided with a transverse groove 156 at the underside of the tab which is arranged to receive a rail 144. Also, a vertical hole 158 is provided in each tab for receiving a threaded fastener 162. The fastener may be turned down into a threaded hole 164 of a discoid nut 166 positioned under rail 144 so that when the fastener 162 is tightened to the nut, the slide 152 is adjustably clamped to the rails 144 of the rack as shown in FIG. 4.

Slide 152 is arranged to support a blade 168 made of a resilient material such as silicone rubber. Blade 168 has a flange 1.68a extending along a longitudinal edge thereof which is slidably received in the slide 152 as shown in FIG. 10B. Slots or slits 170 may be provided in blade 168 into which the instruments $I_s$ may be inserted to stably support the instruments as shown in FIG. 4. Specifically illustrated there are three such supports 148 supporting a plurality of such instruments Is, one of the supports 148 being anchored to the inclined rail segments 146.

In some cases, it may be desirable to place within case 10 a tray whose size may be different from the ones depicted in FIGS. 3A to 3E. For example, such a tray may be slightly shorter and narrower than the tray 42a depicted in FIG. 3A. Accordingly, my system includes a plurality of the brackets 182 depicted in FIGS. 14A and 14B. Each such bracket comprises a relatively long, generally U-shaped channel member 184 having a series of spaced-apart posts 186 projecting rearwardly from the bridging portion of the channel. Each post has a reduced diameter neck or groove 186a for receiving a locking ring 36 described above. The brackets 186 are arranged to be positioned vertically in case 10, with the posts being engaged in one of the vertical columns of holes 16 in a side or end wall of case 10. In use, the legs of the channel member 184 may be cut with scissors or other such tool as shown at 188 so that the channel member will conform to and snugly engage the walls of the tray being supported by supports 182.

The location of the shoulders 188 along the channel member, of course, also determines the height in case 10 of the particular tray being supported by supports 182.

FIGS. 17A and 17B show a bracket 202 for fixating an instrument within case 10 or within the trays in that case. The bracket is a molded plastic part similar to divider 92 in FIGS. 11A and 11B. The bracket has a blade 204 extending up from a base 205 so that it has the shape of an inverted letter T. Posts 206 are spread apart along the length of the base a distance corresponding to the spacing of the holes 54 in trays 42 and the holes 16 in case 10. Each post has a reduced diameter neck or groove 206a for attachment of a locking ring 36 described above. Like divider 92, bracket 202 may be made in a standard length or may be dividable along its length.

Bracket 202 differs from divider 92 in that it's blade 204 has a hole or a notch 208 extending down from the top of the blade, the notch being sized to receive a portion of a surgical instrument to be fixated.

FIGS. 18A and 18B illustrate a similar fixating bracket 210 composed of a pair of spaced-apart parallel blades 212a and 212b extending up from a base 214. Posts 216, similar to posts 206, extend down from base 214. One of the blades, e.g., blade 212b, has a hole or a notch as shown at 218 to receive a portion of a surgical instrument.

Brackets 202 and 210 are usually used in pairs to limit the motion of the instrument supported by the brackets.

Thus, FIG. 19A shows a pair of brackets 202 supporting a scalpel SC. The position of the scalpel is fixed in the Y coordinate direction. In FIG. 19B, a barrel-shaped instrument BA is retained in the notches 128 of a pair of brackets 210. Thus, motion of the instrument in the X and Y coordinate directions is prohibited. FIG. 19C illustrates a pair of brackets 202, 210 supporting a screwdriver-shaped instrument SI. The shank of the instrument is received in a hole 208 in the blade 204 of bracket 202; the handle of the instrument is received in the blade 212b of bracket 210. This bracket combination prevents displacement of the instrument in the X, Y and Z coordinate directions.

The brackets 202 and 210 may be formed with one notch or hole or a plurality of same depending upon the length of the bracket. Thus, by employing the brackets in various combinations, a variety of different instruments may be fixated in my system.

It is a feature of this invention that the same system used to sterilize, deliver and present medical instruments to the operating theater before an operation can also be used to remove contaminated instruments from that theater after the operation. For this, the system includes a liner 192 made of a lightweight, somewhat flexible material, e.g., polypropylene, for case 10 as shown in phantom in FIG. 4. After a surgical procedure, the liner 192 may be placed in case 10 to cover substantially all the holes 16 therein and the contaminated instruments used in that procedure placed in the lined case 10 for removal to a suitable washer/sterilizer. In this way, workers handling the used instruments after an operation are not likely to be affected by the contaminated instruments.

It will thus be seen that the objects set forth above, among those made apparent from the preceding description, are efficiently attained. Also, certain changes may be made in the above construction without departing from the scope of the invention. For example, the locking ring 36 connections of the various bracket and fixture posts may be substituted for by threaded fasteners screwed into the ends of the posts. Therefore, it is intended that all matter contained in the above description or shown in the accompanying drawings shall be interpreted as illustrative and not in a limiting sense.

It is also to be understood that the following claims are intended to cover all of the generic and specific features of the invention described herein.

Having described my invention, what is claimed as new and secured by Letters Patent is:

1. A modular sterilization tray system for medical instruments comprising a rigid substantially rectangular case having a pair of opposite side walls, a pair of opposite end walls and a bottom wall;

means defining a plurality of vertical columns of vertically spaced apart uniform size holes in opposite walls of the case;

one or more substantially rectilinear instrument trays for placement in said case, the length and width dimensions of each of said trays being directly related to the spacing of said columns of holes in the case opposite walls such that said one or more trays may be positioned within said case so as to be bracketed by selected columns of holes;

fixation means for positioning in selected holes of the bracketing columns of holes in the case opposite walls for fixing the position of said one or more trays at a selected elevation in said case;

an array of holes in the case bottom wall, and an instrument fixating bracket releasably mounted to a wall of said case, said bracket including a main body, and fastening means connected to said body through a pair of holes in the case.

2. The system defined in claim 1 and further including a perforate cover for said case.

3. The system defined in claim 2 and further including means for releasably securing said cover to said case.

4. The system defined in claim 1 and further including an imperforate liner for said case.

5. The system defined in claim 1 and further including an outer wrap for said case, said wrap being permeable to fluid sterilant but impermeable to micro-organisms.

6. The system defined in claim 1 wherein one of said trays occupies substantially the entire interior area of said case.

7. The system defined in claim 1 wherein at least one of said trays occupies substantially one-half the length of said case.

8. The system defined in claim 1 wherein at least one of said trays occupies substantially one-third the length of said case.

9. The system defined in claim 1 wherein at least one of said trays occupies substantially two-thirds the length of said case.

10. The system defined in claim 1 wherein at least one of said trays occupies substantially one-half the width of said case.

11. The system defined in claim 1 wherein at least one of said trays occupies substantially one-third the width of said case.

12. The system defined in claim 1 wherein at least one of said trays occupies substantially two-thirds the width of said case.

13. The system defined in claim 1 wherein said bracket main body includes a blade, and said fastening means are spaced along an edge of said blade.

14. The system defined in claim 13 wherein said fastening means include posts extending through said pair of holes, and clips releasably engaging said posts.

15. The system defined in claim 13 wherein said blade has an instrument-receiving opening therein.

16. The system defined in claim 15 wherein said blade is of a flexible resilient material.

17. The system defined in claim 1 wherein said fixation means comprise a tray-supporting bracket releasably mounted to a side wall of said case, said bracket including a main body, and fastening means connected to said body through a pair of holes in said case side wall.

18. The system defined in claim 1 wherein said one or more trays each have a bottom wall, and an array of holes in said bottom wall composed of columns and rows of holes which may be aligned with said columns of holes in the case opposite walls.

19. The system defined in claim 1 and further including an instrument-fixating bracket releasably mounted to the bottom wall of said one or more trays, said bracket including a main body, and fastening means connected to said body through at least one of said holes in the tray bottom wall.

20. The system defined in claim 1 wherein said bracket main body includes a blade, and said fastening means are spaced along an edge of said blade.

21. A modular sterilization tray system for medical instruments comprising a rigid, substantially rectangular case having a pair of opposite side walls, a pair of opposite end walls and a bottom wall;

means defining a plurality of vertical columns of vertically spaced apart holes in opposite walls of the case;

means defining an array of holes in the bottom wall of the case;

one or more substantially rectilinear instrument trays for placement in said case, each of said trays having a bottom wall, the length and width dimension of each of said trays being related directly to the spacing of said columns of holes in the case opposite walls such that said one or more trays may be positioned within said case so as to be bracketed by selected columns of holes, and an instrument-fixating bracket releasably mounted to a said bottom wall, said bracket including a main body, and fastening means connected to said main body and releasably connected to a said bottom wall.

22. The system defined in claim 1 wherein said bracket main body includes a blade with an edge, and said fastening memos include a pair of posts extending frown said blade through a pair of said holes in a said bottom wall, and clips releasably engaging said post on the opposite side of said bottom wall from said bracket main body.

23. The system defined in claim 1 wherein said blade has an instrument-receiving opening therein.

24. The system defined in claim 23 wherein said instrument-receiving opening is a slit or notch which extends generally perpendicular to the edge of the blade.

25. The system defined in claim 21 wherein said bracket main body includes a pair of laterally spaced apart blades, at least one of which has an instrument-receiving opening therein.

26. The system defined in claim 25 wherein said opening is a slit or notch which extends generally perpendicular to the edge of said one blade.

27. The system defined in claim 21 wherein said main body is a peg, and said fastening means are located at an end of the peg and are retained in a hole in said bottom wall.

28. The system defined in claim 21 wherein said bracket main body includes a pair of spaced-apart posts and a resilient bridging member extending between and connected to said posts, said bridging member having an instrument-receiving opening therein, and said fastening means are located at corresponding ends of said post and are adapted to be received in similarly spaced-apart holes in a said bottom wall.

29. The system defined in claim 21 wherein said bracket main body includes a pair of spaced apart parallel rails, at least one blade extending between said rails and means for adjustably connecting the opposite ends of said at least one blade to said pair of rails, and said fastening means are located at the opposite ends of said pair of rails and are arranged to be received in holes in said base.

\* \* \* \* \*